United States Patent [19]

Cormier et al.

[11] Patent Number: 5,160,741
[45] Date of Patent: * Nov. 3, 1992

[54] REDUCTION OR PREVENTION OF SKIN IRRITATION BY DRUGS

[75] Inventors: Michel J. N. Cormier; Philip W. Ledger, both of Mountain View; Alfred Amkraut, Palo Alto, all of Calif.

[73] Assignee: ALZA Corporation, Palo Alto, Calif.

[ * ] Notice: The portion of the term of this patent subsequent to Jul. 14, 2009 has been disclaimed.

[21] Appl. No.: 793,932

[22] Filed: Nov. 13, 1991

Related U.S. Application Data

[63] Continuation of Ser. No. 549,584, Jul. 6, 1990, Pat. No. 5,130,139.

[51] Int. Cl.$^5$ ............................................. A61R 37/22
[52] U.S. Cl. ................................... 424/450; 424/449; 424/448
[58] Field of Search ................. 424/448, 449, 450, 456

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 3,991,755 | 11/1976 | Vernon et al. | 128/172.1 |
| 4,141,359 | 2/1979 | Jacobsen et al. | 128/172.1 |
| 4,250,878 | 2/1981 | Jacobsen et al. | 128/207.21 |
| 4,274,420 | 6/1981 | Hymes | 128/641 |
| 4,286,592 | 9/1981 | Chandrasekaran | 128/260 |
| 4,314,557 | 2/1982 | Chandrasekaran | 128/260 |
| 4,325,367 | 4/1982 | Tapper | 128/207.21 |
| 4,379,454 | 4/1983 | Campbell et al. | 424/448 |
| 4,391,278 | 7/1983 | Cahalan et al. | 128/640 |
| 4,398,545 | 8/1983 | Wilson | 128/798 |
| 4,419,092 | 12/1983 | Jacobsen et al. | 604/20 |
| 4,474,570 | 10/1984 | Ariura et al. | 604/20 |
| 4,557,723 | 12/1985 | Sibalis | 604/20 |
| 4,559,222 | 12/1985 | Enscore et al. | 424/28 |
| 4,573,995 | 3/1986 | Chen et al. | 604/896 |
| 4,640,689 | 2/1987 | Sibalis | 604/20 |
| 4,702,732 | 10/1987 | Powers et al. | 604/20 |
| 4,708,716 | 11/1987 | Sibalis | 604/20 |
| 4,855,294 | 8/1989 | Patel et al. | 514/212 |
| 4,885,154 | 12/1989 | Cormier et al. | 424/10 |
| 4,908,213 | 3/1990 | Govil et al. | 424/447 |
| 4,983,395 | 1/1991 | Chang et al. | 424/449 |

FOREIGN PATENT DOCUMENTS 0267051 5/1988 European Pat. Off. .
2124485B 2/1984 United Kingdom .

OTHER PUBLICATIONS

Cramb, Biochem. Pharmacol. 35: 1365–1372 (1986).
Hollemans et al., Biochim. Biophys. Acta 643: 140–151 (1981).
MacIntyre et al., Biopharm. & Drug Disposition 9:513–526 (1988).
Maxfield, J. Cell Biol. 95:676–681 (1982).
Ohkuma et al., Proc. Natl. Acad. Sci. USA 75:3327–3331 (1978).
Pressman, Chapter 6, in, Eichhorn (ed.) "Inorganic Biochemistry", vol. 1, pp. 203–226, Elsevier Scientific Publishing Co., New York, 1973.
Reijngoud et al., FEBS Letters 64:231–235 (1976).
Swisher et al., Models Dermatol. Basel, Karger, 4:131–137 (1989).
Vestal et al., J. Pharmacol. Exp. Therap. 214:106–111 (1980).

*Primary Examiner*—Thurman K. Page
*Assistant Examiner*—Leon R. Horne
*Attorney, Agent, or Firm*—Jacqueline S. Larson; Edward L. Mandell; Steven F. Stone

[57] ABSTRACT

The present invention provides a method of reducing or preventing skin irritation of a weak base drug by inhibiting the accumulation of the drug in the lysosomes. The drug is irritating to humans, i.e., the drug is susceptible to inducing skin or mucosa irritation in a human when the drug is transdermally administered to the human at a therapeutically effective rate. Irritation reduction or prevention is induced by coadministering to the skin or mucosa of the human:

(a) a therapeutically effective amount of a weak base drug which is irritating to humans, at a therapeutically effective rate over a predetermined period of time; and (b) an effective amount of an agent capable of inhibiting the lysosomal uptake of the drug to reduce or prevent irritation to the skin or mucosa.

25 Claims, 3 Drawing Sheets

REDUCTION OR PREVENTION OF SKIN IRRITATION BY DRUGS

This application is a continuation of application Ser. No. 07/549,584) filed Jul. 6, 1990, U.S. Pat. No. 5,130,139, and benefit of the filing date of said earlier filed application is claimed under 35 U.S.C. §120.

CROSS-REFERENCE TO RELATED APPLICATIONS

This invention is related to the inventions disclosed in the copending, coassigned patent applications Ser. No. 07/217,014 filed on Jul. 8, 1988, U.S. Pat. No. 5,000,956 of Amkraut et al., for Prevention of Contact Allergy by Coadministration of a Corticosteroid with a Sensitizing Drug; and Ser. No. 07/364,932 filed on Jun. 9, 1989, U.S. Pat. No. 5,049,387 of Amkraut, for Inducing Skin Tolerance to a Sensitizing Drug.

FIELD OF THE INVENTION

This invention relates to the transdermal delivery of drugs. More particularly, this invention relates to the reduction or elimination of skin irritation caused by the accumulation of certain irritating drugs in intracellular vesicles such as the lysosomes.

DESCRIPTION OF TERMS

The term "drug", as used herein, refers to a biologically active agent, compound or composition of matter which is administered for the purpose of providing some beneficial or therapeutic effect.

As used herein, the term "transdermal" delivery or administration refers to the delivery or administration of agents by passage through skin, mucosa and/or other body surfaces by topical application or by iontophoresis.

The term "weak base", as used herein, refers to a basic compound having at least one $pK_a$ greater than 4.5.

BACKGROUND OF THE INVENTION

The transdermal route of parenteral drug delivery provides many advantages. Unfortunately, however, many drugs which are candidates for transdermal delivery have a tendency to cause skin irritation to human patients, particular when they are maintained in contact with the skin under occlusion for sustained periods of time. These irritating drugs can cause undesirable skin reactions, such as itching and erythema. Therefore, despite the development of the transdermal drug delivery art, there remains a continuing need for an improved method of overcoming irritation caused by transdermal delivery of an irritating drug.

Skin irritation can be caused by a variety of factors including, but not limited to, physical factors (e.g., chafing or occluding the skin in an airtight manner), exposure to certain chemicals, exposure to pH outside the normal pH range of the skin or mucosa, and bacterial overgrowth. Generally, tissue irritation is the manifested result of damage or toxicity to cells in the skin or mucosa caused by their response to a cytotoxic (i.e., irritating) agent.

Investigators have found that amphiphilic weak bases tend to accumulate extensively in body tissues. While this is due in part to the interaction such compounds with membranes, it is also due to a large extent to the fact that weak bases accumulate in lysosomes as a result of the low intralysosomal pH (MacIntyre et al., Biopharm. & Drug Disposition, 9:513–526 (1988); Hollemans et al., Biochim. Biophys. Acta, 643:140–151 (1981)).

Lysosomes are small membrane-enclosed organelles which are found within almost all animal cells. Under normal conditions, lysosomes have an internal pH in the range of 4.5 to 5. In contrast, the physiological pH outside the cell is about 7.0. This difference results in extensive accumulation within the lysosome of weak bases. The weak bases can permeate the cell and the lysosomal membranes in their uncharged molecular form. However, the low internal pH of lysosomes favors protonation of the weak base molecules; once they are charged, the molecules are relatively membrane-impermeable and less able to pass back through the membrane.

Several important drugs are weak bases and have been shown to accumulate in lysosomes. These drugs include, for example, the betaadrenergic antagonist propranolol (Cramb, Biochem. Pharmacol., 35:1365–1372 (1986)) and the antimalarial drug chloroquine (Reijngoud et al., FEBS Letters, 64:231–235 (1976)). The accumulation of these weak bases can be inhibited by competition using other amphiphilic amines by virtue of the fact that weak bases raise the pH in the lysosome (Maxfield, J. Cell Biol., 95:676–681 (1982); Ohkuma et al., Proc. Natl. Acad. Sci. USA, 75:3327–3331 (1978)).

Other compounds, the ionophores, have also been shown to raise the pH in lysosomes (Maxfield, ibid.; Ohkuma et al., ibid.). The ionophores incorporate in the lysosomal membranes and facilitate the exchange of ions, thereby destroying the normally-existing pH gradient (Pressman, "Alkali Metal Chelators—The Ionophores", in, Eichhorn, ed., Inorganic Biochemistry, Vol. 1, pp. 218–221, Elsevier Scientific Publishing Co., N.Y., 1973).

SUMMARY OF THE INVENTION

The inventors have now found that there is a direct correlation between the cytotoxicity of certain drugs and the amount of the drug present in the cellular lysosomes. Thus, the greater the accumulation of a drug in the cell, the more toxic it is. The inventors have also observed that the inhibition of accumulation in the lysosomes results in the reduction of the cytotoxicity of the drug, so that the toxicity of a drug that is normally accumulated can be reduced by inhibiting its uptake. Since one of the main causes of irritation associated with transdermal delivery of drugs is the damage done to the cell by the cytotoxic effects of agents, inhibiting the accumulation of large amounts of the cytotoxic agent in the lysosomes should result in the reduction or avoidance of skin irritation.

Therefore, it is an object of the present invention to reduce or present skin irritation in a human patient caused by the transdermal administration to the patient of an irritating weak base drug.

It is a further object of the present invention to reduce or prevent skin irritation in a human patient caused by the transdermal administration of an irritating weak base drug by inhibiting the lysosomal uptake of the irritating weak base drug.

These and other objects, features and advantages are met by the present invention which provides a method of reducing or preventing skin irritation by inhibiting the accumulation of a weak base drug in the lysosomes. The drug is irritating to humans, i.e, the drug is susceptible to inducing skin or mucosa irritation in a human when the drug is transdermally administered to the human at a therapeutically effective rate. Skin irritation reduction or prevention is induced by coadministering to the skin or mucosa of the human:

(a) a therapeutically effective amount of a weak base drug which is irritating to humans, at a therapeutically effective rate over a predetermined period of time; and (b) an effective amount of an agent capable of inhibiting the lysosomal uptake of the drug to reduce or prevent irritation to the skin or mucosa.

The system of the invention comprises a matrix adapted to be placed in a weak base drug and lysosomal uptake-inhibiting agent transmitting relation with the selected skin or mucosa site. The matrix contains sufficient amounts of the drug and the agent to continuously coadminister to the skin or mucosa site the drug, at a therapeutically effective rate and over a predetermined delivery period; and the lysosome uptake-inhibiting agent, in an amount and for a period of time sufficient to inhibit the accumulation of the drug in the lysosomes. A device for carrying out the invention may be either a passive transdermal device or an active transdermal device where transport of the agent is assisted by electric, sonic, thermal or other energy source.

DETAILED DESCRIPTION OF THE INVENTION

According to the present invention, transdermal coadministration of a normally irritating weak base drug with a lysosomal uptake-inhibiting agent reduces or prevents skin irritation in humans by inhibiting the accumulation of the irritating drug in the lysosomes.

The present invention is applicable to any chemical agent or drug which tends to accumulate at relatively high concentrations in cellular lysosomes and causes skin irritation to a human as a result of such accumulation. These are weak bases having at least one $pK_a$ greater than 4.5. Included within this group are therapeutically important drugs such as, but not limited to, antidepressants, such as imipramine, desipramine and nortriptyline; antihistamines, such as clemastine, chlorpheniramine and diphenhydramine; antineoplastics, such as daunorubicin; antimalarials, such as chloroquine and quinacrine; antipsychotics, such as chlorpromazine, fluphenazine and perphenazine; beta blocking drugs, such as propranolol, alprenolol, labetalol, metoprolol, timolol, pindolol and atenolol; local anesthetics, such as tetracaine, lidocaine and prilocaine; opiate agonists, such as buprenorphine and sufentanil; opiate antagonists, such as naloxone and naltrexone; sympatholytics, such as phentolamine; sympathomimetics, such as phenylpropanolamine, ephedrine, mephentermine and bitolterol; vasodilating agents, such as tolazoline; and aminoglycoside antibiotics, such as streptomycin and gentamycin.

Accumulation of a given weak base drug into the lysosomes can be inhibited in at least two different ways. The first is through the action upon lysosomal membranes by an agent that interferes with ion pumps and thereby allows the intralysosomal pH to rise, destroying the pH gradient and lessening the tendency to ionize drugs that may enter. Examples of such interfering agents are the ionophores, such as monensin, (R)(+)-1,1'-bi-2-naphthol, nigericin, valinomycin, gramicidin D, A23187, X537A, and carbonyl cyanide m-chlorophenylhydrazone. The second mode of action is the competition by other basic molecules with the drug for uptake and available charge in the low pH lysosomal micro-environment. These competitive weak bases also raise the pH within the lysosomes as they accumulate. Examples of such competitors are amphiphilic cations and include amphiphilic amines, such as ammonia and its salts (ammonium chloride being an example), low molecular weight amines (such as methylamine, diethylamine and isopropylamine) and their salts, and aminoalcohols (such as ethanolamine, diethanolamine, triethanolamine and tromethamine) and their salts. In a presently preferred embodiment, competitor compounds, and particularly the amphiphilic amines, are preferred as the uptake-inhibiting agent.

The lysosomal uptake-inhibiting agents can be selected from those exhibiting one or the other or both of the above two modes of action, or they may be selected from other compounds that work by otherwise raising the intralysosomal pH or by mechanisms not presently known. The basic requirement of a lysosomal uptake-inhibiting agent under the present invention is that it inhibit the accumulation of the irritating weak bas drug in the lysosome.

In this invention, the lysosomal uptake-inhibiting agent is continuously and co-extensively administered with the weak base drug and to the same skin or mucosa as the drug in an amount sufficient to reduce or eliminate irritation by the drug in the human. For any given drug and uptake-inhibiting agent combination, the amount can be experimentally determined following the procedures outlined in the Examples herein.

In one embodiment of the invention, the uptake-inhibiting agent should be coadministered with the drug throughout all or almost all of the time period during which the drug is administered. This is particularly the case when the agent, once removed from the treatment site, quickly loses its inhibiting action; that is, once the agent is removed, the internal pH within the lysosomes will being to return to its normal lower level and as the pH loweres, the drug will begin to accumulate in the lysosomes to a toxic level, causing irritation in the patient. This is of particular concern when administration takes place over a relatively long period of time, such as greater than 24 hours. In another embodiment of the invention, continuous coadministration of the drug and an uptake-inhibiting agent is not required when the agent continues to exert an action on the lysosomes for an extended period after it is removed from the treatment site. In such cases, the drug and the agent are coadministered to a site for a sufficient period of time to cause inhibition of accumulation of drug in the lysosomes, adapter which time the drug alone may continue to be administered to the site.

In addition to coadministering the uptake-inhibiting agent during administration of the drug, it is desirable in some instances to pretreat the skin or mucosal administration site with the agent prior to application of the drug. This pretreatment will depend on the particular uptake-inhibiting agent chosen as well as the drug to be used. In this manner, the lysosomal pH will have been sufficiently altered to inhibit drug uptake before the drug is present. Pretreatment with the agent is especially useful when the agent is slow to affect the lysosomal pH or when the drug has a very rapid rate of accumulation within the lysosome.

According to the present invention, one or more lysosomal uptake-inhibiting agents and the irritating weak base drug are placed in drug and uptake-inhibiting agent transmitting relation with the appropriate body surface, preferably suspended in a carrier therefor, and maintained in place for the desired period of time. The drug and agent are typically dispersed within a physiologically compatible matrix or carrier which may be applied directly to the body as an ointment, gel, cream, suppository or sublingual or buccal tablet, for example, or they may be administered from a matrix or carrier in a transdermal therapeutic delivery device or an iontophoretic delivery device.

The transdermal route of parenteral delivery of drug provides many advantages, and transdermal therapeutic devices for delivering a wide variety of drugs or other beneficial agents are well known in the art. Typical deices are described in U.S. Pat. No. 3,598,122, 3,598,123, 4,286,592, 4,314,557, 4,379,454, 4,559,222 and 4,573,995, for example, al of which are incorporated herein by reference. The coadministration of a lysosomal uptake-inhibiting agent and a drug as disclosed herein can be accomplished using transdermal devices of these kinds.

In order to ensure co-extensive administration of drug and lysosomal uptake-inhibiting agent to skin or mucosa, it is preferred to administer the drug and agent from a matrix (e.g., a drug- and agent-containing matrix) in a transdermal delivery device, which matrix is placed in drug and uptake-inhibiting agent transmitting relation with the skin or mucosa.

Figure 1:
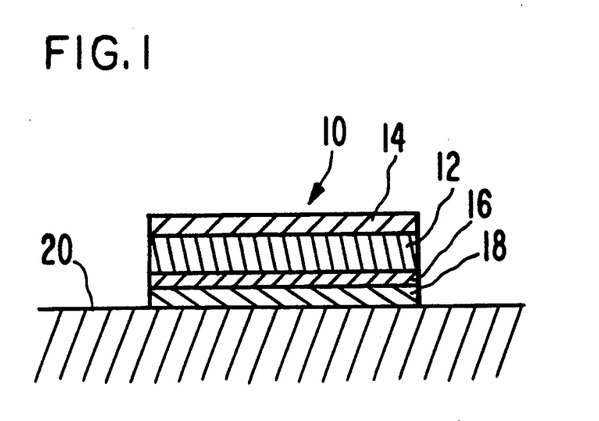
FIG. 1 is a cross-sectional view of one embodiment of a transdermal therapeutic drug delivery device which may be used in accordance with the present invention.
Figure 2:
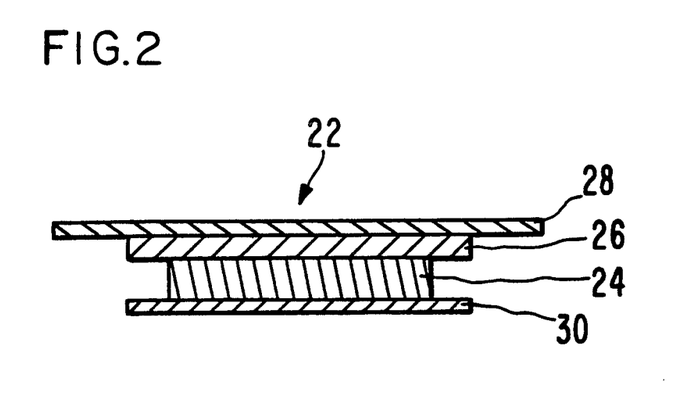
FIG. 2 is a cross-sectional view of another embodiment of a transdermal therapeutic drug delivery device which may be used in accordance with the present invention.

Two examples of suitable transdermal delivery devices are illustrated in FIGS. 1 and 2. In FIG. 1, transdermal delivery device 10 comprises a reservoir 12 containing both a weak base drug and a lysosomal uptake-inhibiting agent. Reservoir 12 is preferably in the form of a matrix containing the drug and agent dispersed therein. Reservoir 12 is sandwiched between a backing layer 14, which is impermeable to both the drug and the agent, and a rate-controlling membrane 16. In FIG. 1, the reservoir 12 is formed of a material, such as a rubbery polymer, that is sufficiently viscous to maintain its shape. If a lower viscosity material is used for reservoir 12, such as an aqueous gel, backing layer 14 and rate-controlling membrane 16 would be sealed together about their periphery to prevent leakage. The device 10 adheres to the surface of the skin 20 by means of an in-line contract adhesive layer 18. The adhesive layer 18 may optionally contain agent and/or drug. A strippable release liner (not shown) is normally provided along the exposed surface of adhesive layer 18 and is removed prior to application of device 10 to the skin 20.

Alternatively, as show in FIG. 2, transdermal therapeutic device 22 may be attached to the skin or mucosa of a patient by means of an adhesive overlay 28. Device 22 is comprised of a drug- and agent-containing reservoir 24 which is preferably in the form of a matrix containing the drug and the agent dispersed therein. An impermeable backing layer 26 is provided adjacent one surface of reservoir 24. Adhesive overlay 28 maintains the device on the skin and may be fabricated together with, or provided separately from, the remaining elements of the device. With certain formulations, the adhesive overlay 28 may be preferable to the in-line contact adhesive 18 as shown in FIG. 1. This is true, for example, where the drug/agent reservoir contains a material (such as, for example, an oily surfactant permeation enahancer) which adversely affects the adhesive properties of the in-line contact adhesive layer 18. Impermeable backing layer 26 is preferably slightly larger than reservoir 24, and in this manner prevents the materials in reservoir 24 from adversely interacting with the adhesive in overlay 28. Optionally, a rate-controlling membrane (not shown in FIG. 2) similar to membrane 16 in FIG. 1 may be provided on the skin/mucosa side of reservoir 24. A strippable release liner 30 is also provided with device 22 and is removed just prior to application of device 22 to the skin.

In those cases where it is desired to pretreat the skin or mucosa with the lysosomal uptake-inhibiting agent prior to coadministration of drug/agent or where the drug flux is much grater than the agent flux, an amount of the agent may be present in the adhesive layer 18. On the other hand, where it is not necessary to pretreat the application site or where there is no great disparity between drug and agent fluxes, both the drug and the agent may be delivered from the adhesive layer 18 as well as from the reservoir 24.

The drug and the lysosomal uptake-inhibiting agent can be coextensively administered to human skin or mucosa by direct application to the skin or mucosa in the form of am ointment, gel, cream or lotion, for example, but is preferably administered from a skin patch or other known transdermal delivery device which contains a saturated or unsaturated formulation of the drug and the agent. The formulation may be aqueous or non-aqueous based. The formulation should be designed to deliver the weak base drug and the uptake-inhibiting agent at the necessary fluxes. Depending on the drug to be delivered, the drug and agent carriers(s) may be either aqueous or non-aqueous based. Aqueous formulations typically comprise water and about 1-2 weight % of a hydrophilic polymer as a gelling agent, such as hydroxyethylcellulose or hydroxypropylcellulose. Typical non-aqueous gels are comprised of silicone fluid or mineral oil. Mineral oil-based gels also typically contain 1-2 weight % of a gelling agent such as colloidal silicon dioxide. The suitability of a particular gel depends upon the compatability of its constituents with both the weak base drug and the lysosomal uptake-inhibiting agent, along with a permeation enhancer, if one is present, and may other components in the formulation.

The reservoir matrix should be compatible with the drug, the uptake-inhibiting agent and any carrier therefor. When using an aqueous-based system, the reservoir matrix is preferably a hydrophilic polymer, e.g., a hydrogel. When using a non-aqueous-based system, the reservoir matrix is preferably comprised of a hydrophobic polymer. Suitable polymeric matrices are well known in the transdermal drug delivery art, and examples are listed in the above-named patents previously incorporated herein by reference.

When a constant drug delivery rate is desired, the weak base drug is present in the matrix or carrier at a concentration in excess of saturation, the amount of excess being a function of the desired length of the drug delivery period of the system. The drug may, however, be present at a level below saturation without departing from this invention as long as the drug and the uptake-inhibiting agent are continuously and co-extensively administered to the same skin or mucosa site in an amount and for a period of time sufficient to reduce or eliminate skin irritation by the drug.

In addition to the irritating weak base drug and the lysosomal uptake-inhibiting agent, which are essential to the invention, the matrix or carrier may also contain dyes, pigments, inert fillers, permeation enhancers (for either the drug or the uptake-inhibiting agent or for both), excipients and other conventional components of pharmaceutical products or transdermal devices known in to the art.

Drugs may also be delivered transdermally by iontophoresis, and iontophoretic devices for delivering a wide variety of drugs or other beneficial agents are well known in the art. Iontophoretic delivery devices include a donor electrode assembly which includes a donor electrode and a reservoir containing the beneficial agent to be iontophoretically delivered. The donor electrode assembly is adapted to be placed in agent transmitting relation with the skin or mucosa of the patient. The device also includes a counter electrode assembly adapted to be placed in electrical contact with the skin at a location spaced apart from the donor electrode. Further, the device includes an electric power source. The electrodes and the power source are electrically connected and form a closed circuit when the electrode assemblies are placed in current conducting relation with the skin of the patient. The coadministration of a lysosomal uptake-inhibiting agent and a drug as disclosed herein can be accomplished using any iontophoretic device. Typical devices are described in U.S. Pat. Nos. 3,991,755, 4,141,359, 4,250,878, 4,274,420, 4,325,367, 4,391,278, 4,398,545, 4,419,092, 4,474,570, 4,557,723, 4,460,689, 4,702,732 and 4,708,716, for example, all of which are incorporated herein by reference.

Figure 5:
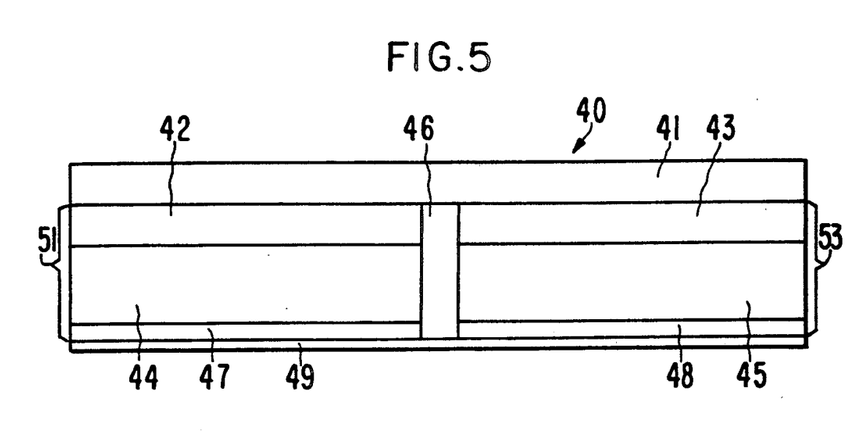
FIG. 5 is a schematic view of an iontophoretic drug delivery device which may be used in accordance with the present invention.

FIG. 5 illustrates one example of a preferred iontophoretic delivery device 40. Device 40 has a top layer 41 which contains an electrical power supply (e.g., a battery or a series of batteries) as well as optional control circuitry such as a current controller (e.g., a resistor or a transistor-based current control circuit), an on/off switch, and/or a microprocessor adapted to control the current output of the power source over time. Device 40 also includes electrode assembly 51 and electrode assembly 53. Electrode assemblies 51 and 53 are separated from one another by an electrical insulator 46 and form therewith a single self-contained unit. For purposes of illustration, the electrode assembly 51 will be referred to as the "donor" electrode assembly while electrode assembly 53 will be referred to as the "counter" electrode assembly. In this embodiment, the donor electrode 42 is positioned adjacent drug reservoir 44 while the counter electrode 43 is positioned adjacent the return reservoir 45 which contains an electrolyte. Electrodes 42 and 43 are formed from metal foils (such as silver or zinc) or a polymer matrix loaded with metal powder, powdered graphite, carbon fibers or any other suitable electrically conductive material. Reservoirs 44 and 45 can be polymeric matrices or gel matrices. Insulator 46 is composed of a non-electrical conducting and non-ion-conducting material which acts as a barrier to prevent short-circuiting of the device 40. Insulator 46 can be an air gap, a non-ion-conducting polymer or adhesive or other suitable barrier to ion flow. The device 40 is adhered to the skin by means of ion-conducting adhesive layers 47 and 48. The device 40 also includes a strippable release liner 49 which is removed just prior to application to the skin.

In a typical device 40, the drug reservoir 44 contains an ionizable supply of the drug to be delivered together with the lysosomal uptake-inhibiting agent, and the counter reservoir 45 contains a suitable electrolyte. In this way, the positive drug ions are delivered through the skin from the anode electrode assembly. The drug reservoir 44 of the iontophoretic delivery device 40 must be in drug and uptake-inhibiting agent relation with the skin or mucosa. It is not necessary, however, that the return reservoir 45 be in electrolyte transmitting relation with the skin or mucosa, although that is preferred. It has been found to be preferable to use a water-soluble salt of the drug or agent to be delivered.

In the present invention, the drug is delivered at a therapeutically effective rate and the agent is delivered at a lysosomal uptake-inhibiting rate(s), for a predetermined time period. The relevant time frame varies with the regimen of drug administration involved. Some drugs must be administered continuously for one or more days. In that instance, a suitable transdermal device would have sufficient drug and lysosomal uptake inhibitor to provide the necessary rate of delivery of up to 24 hours for devices that are replaced periodically or of up to a week for longer-duration devices. Some drugs are only administered once and in that instance, a suitable device would have sufficient drug and uptake inhibitor to provide the necessary rates of delivery for a few hours.

The minimum required administration amount and rate of the lysosomal uptake-inhibiting agent in the present invention depends upon a number of factors including the type and amount of weak base drug being administered, the period of time over which the drug and the agent are coadministered, the type of action exhibited by the agent, (e.g., whether it is interfering or competing with drug uptake in the lysosome), and the potency of the agent. Typically, all other variables being equal, the concentrations of competitor compounds that are required will be higher than the concentration of ionophores, since their mechanism of action is by competition. Thus, the amount of competitor uptake-inhibiting agent required to inhibit the accumulation of a weak base drug in the lysosomes is from about 0.2 wt % (weight percent) to about 20 wt % of the drug/agent composition, whereas the amount of ionophore uptake-inhibiting agent required is from about 0.01 wt % to abut 5 wt %.

The following examples are offered to illustrate the practice of the present invention. It is important to note that this invention is not limited to any particular transdermal device or other form of transdermal delivery, as are commonly known in the art. Nor is this invention limited to a particular formulation. Therefore, the embodiments described herein are merely illustrative and are not intended to limit the scope of the invention in any manner. In the following examples, cytotoxic effect is stated as "$ID_{50}$"; that is, the concentration of drug required to kill 50% of the cells.

EXAMPLE 1

Four beta-adrenergic blocking drugs (propranolol, labetalol, pindolol and timolol) were tested for their uptake and their toxicity in human skin fibroblasts.

To estimate the toxicity of the tested compounds, the general procedure of the MTT assay (Swisher et al., Models Dermatol., Maibach and Lowe (eds.), Basel, Karger, vol. 4, pp 131-137, 1989) was used. Cell cultures of fibroblasts were incubated for 16 hours in medium containing a range of concentrations of the drug being tested. At the end of the incubation time, the medium was removed and replaced with medium containing MTT at 0.5 mg/ml. After 3 hours, this medium was discarded and the blue formazan, a metabolite of MTT produced only by viable cells, was dissolved in acidified isopropanol. Absorbance of this solution was measured at 540 nm against a reference wavelength of 660 nm. Results were then expressed as percent of control cultures incubated in the same conditions without drug or agent. The concentration of drug (or drug in the presence of agent) that gave 50% absorbance of the control value was then determined. This concentration is stated as $ID_{50}$; that is, the concentration of the drug required to kill 50% of the cells.

For the uptake studies, cell cultures of fibroblasts were exposed to medium containing the radioactive-labelled drug and incubated for 16 hours. The uptake process was then stopped by removing the medium and rapidly washing the cells with cold PBS three times. The cells were then extracted with methanol which was transferred to counting vials, and the amount of radioactivity was measured by liquid scintillation. To compensate for non-specific binding to the plastic of the wells, wells containing no cells were incubated with the radiolabelled drugs under the same conditions. The radioactive content of those wells was taken as the control value and substracted from the radioactive content of the wells containing cells.

The results showed a strong correlation between the accumulation of each drug in the fibroblast cells and the drug's toxicity (r=0.99). In other words, the greater its accumulation in the cell, the more toxic was the drug.

EXAMPLE 2

The effect of monensin on the accumulation and the toxicity of propranolol was determined.

Fibroblast cell cultures were incubated for 16 hours in propranolol ($2 \times 10^{-7}$ M) with various concentrations of monensin. The accumulation of propranolol in the cells was then determined, following the procedures of Example 1. The monensin decreased propranolol uptake in the cells in a dose-dependent manner from $10^{-8}$ M to $10^{-5}$ M of monensin. At $10^{-5}$ M monensin, propranolol uptake was negligible even though the cells were fully viable.

The treated cells were also tested for the cytotoxic effect of propranolol in the presence of various concentrations of monensin, following the procedures of Example 1. The same range of concentrations of monensin as above tested yielded a dose-dependent decrease of propranolol toxicity from an $ID_{50}$ of $2.8 \times 10^{-4}$ M propranolol without monensin to an $ID_{50}$ of $3.8 \times 10^{-4}$ M propranolol with monensin at $10^{-5}$ M.

EXAMPLE 3

Monensin-induced inhibition of toxicity ($ID_{50}$) with five other weak base drugs was investigated, following the procedures of Example 1. These five drugs were selected because of their high cytotoxicity and published reports indicating their accumulation in cells. They were tested with $10^{-6}$ M monensin. The results are presented in Table A below and show that monensin reduced the toxicity of all the drugs.

In the Table, the "factor of protection" is the ratio of the $ID_{50}$ of the toxic drug incubated with monensin to the $ID_{50}$ of the toxic drug alone.

TABLE A

| Drug | $ID_{50}$(M) Drug Alone | $ID_{50}$(M) Drug + Monensin | Factor of Protection |
|---|---|---|---|
| Clemastine | $1.9 \times 10^{-5}$ | $2.3 \times 10^{-5}$ | 1.2 |
| Imipramine | $1.9 \times 10^{-4}$ | $2.7 \times 10^{-4}$ | 1.4 |
| Chlorpromazine | $1 \times 10^{-5}$ | $1.6 \times 10^{-5}$ | 1.6 |
| Quinacrine | $1.3 \times 10^{-5}$ | $4.2 \times 10^{-5}$ | 3.2 |
| Chloroquine | $7 \times 10^{-5}$ | $7 \times 10^{-4}$ | 10.0 |

EXAMPLE 4

The action of various ionophores and amphiphilic amines on the cytotoxicity of propranolol and chloroquine was determined, following the procedures of Example 1. The results are presented in Table B below. The "factor of protection" corresponds to the ratio of the $ID_{50}$ of the toxic drug incubated with uptake-inhibiting agent at the indicated concentration, to the $ID_{50}$ of the toxic drug alone. The "mode of action" indicates either the ions which are preferentially carried by the tested ionophores or that the agent acts by competition.

TABLE B

| Uptake-Inhibiting Agent | Factor of Protection Chloroquine | Factor of Protection Propranolol | Mode of Action |
|---|---|---|---|
| Monensin ($10^{-5}$M) | 19 | $1.4^1$ | $Na^+$ |
| (R)(+)-1,1'-bi-2-Naphthol ($3.5 \times 10^{-5}$M) | 2.9 | $ND^2$ | $Na^+$ |
| 15-Crown-5 ($10^{-4}$M) | 1 | 1 | $Na^+/K^+$ |
| Nigericin ($1.5 \times 10^{-7}$M) | 11 | ND | $K^+/Na^+$ |
| Valinomycin ($10^{-5}$M) | 13 | 1 | $K^+$ |
| Gramicidin D ($10^{-5}$M) | 31 | 1 | $K^+$ |
| Nonactin ($5 \times 10^{-6}$M) | 26 | 1 | $NH_4^+$ |
| A23187 ($10^{-6}$M) | 11 | 1 | $Ca^{++}$ |
| Carbonyl cyanide m-chlorophenylhydrazone ($10^{-5}$M) | 13 | 1 | $H^+$ |
| Ammonium chloride ($4 \times 10^{-2}$M) | 26 | $1.3^1$ | Competition |
| Diethylamine ($10^{-2}$M) | 3.3 | ND | Competition |
| Isopropylamine ($10^{-2}$M) | 6.2 | ND | Competition |
| Ethanolamine ($10^{-2}$M) | 6.4 | ND | Competition |
| Diethanolamine ($10^{-2}$M) | 1.5 | ND | Competition |
| Tromethamine ($10^{-2}$M) | 1.2 | ND | Competition |
| Triethanolamine ($10^{-2}$M) | 1.3 | ND | Competition |
| Propranolol ($2 \times 10^{-4}$M) | 1.8 | — | Competition |
| Chloroquine ($10^{-5}$M) | — | 1 | Competition |

[1] pre-treatment of 2 hours with the uptake-inhibiting agent
[2] ND = no determination

EXAMPLE 5

The decrease in the in vivo skin irritation of two drugs, chloroquine and propranolol, by the addition of an amphiphilic amine, ammonium chloride, was illustrated as follows.

Either chloroquine (1.0 wt %) or propranolol (2.0 wt %) was formulated in hydroxyethylcellulose (2 wt %) in water in the presence or absence of ammonium chloride (5.0 wt %). The resulting gels were buffered to pH 8.5 with EPPS buffer and contained 30 wt % ethanol to maintain the solubility of the drug.

Figure 3A:
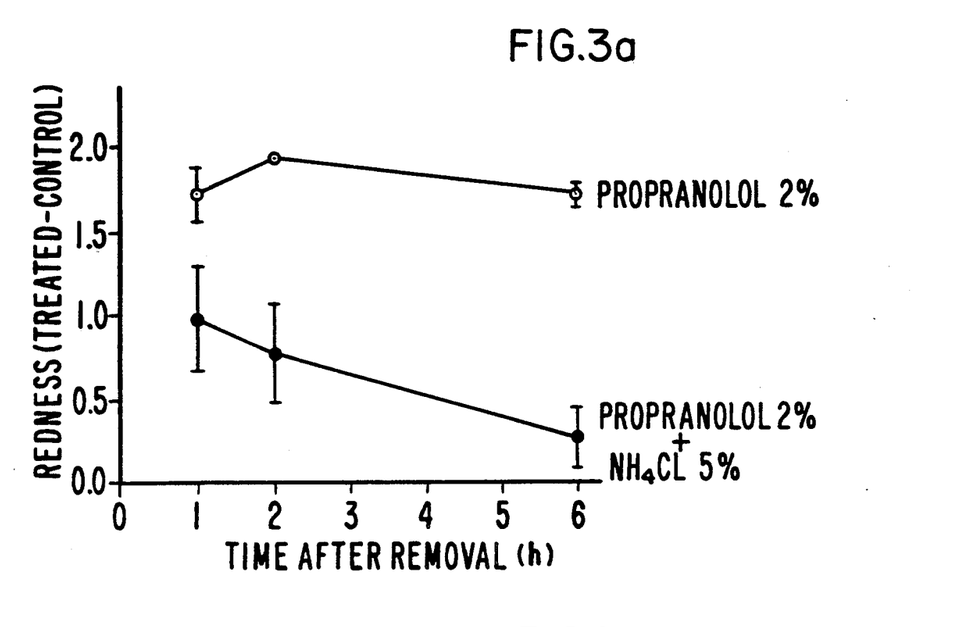
FIGS. 3a and 3b are graphs which show the amount of in vivo skin irritation (erythema) at various times after treatment with propranolol (3a) alone or with ammonium chloride, or after treatment with chloroquine (3b) alone or with ammonium chloride or with monensin.
Figure 3B:
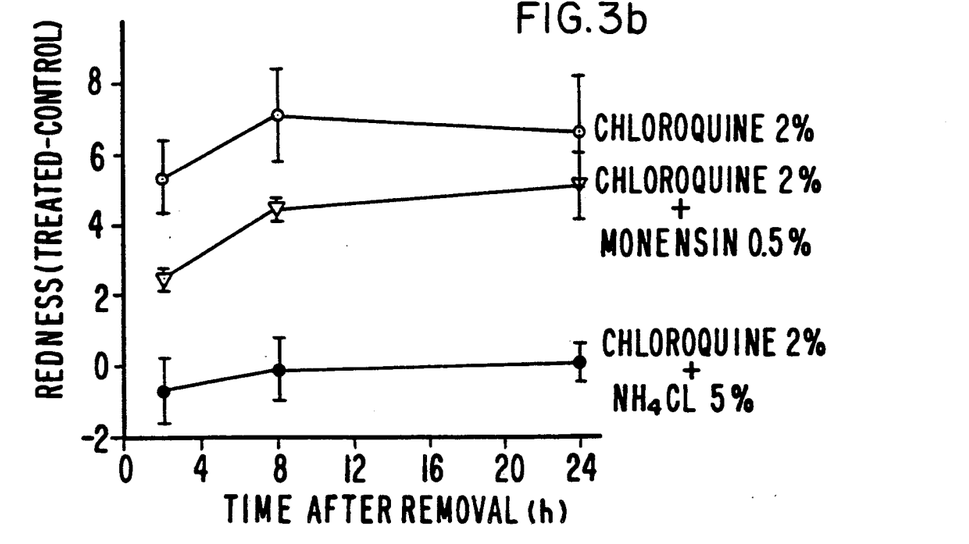

25 Microliters of gel were placed in an aluminum cup and applied in duplicate or triplicate to the volar forearm of an adult male. All of the gels were placed in such manner. After 16 hours, each cup was removed and the site was washed. At various times thereafter the sites were observed and the intensity of the irritant reaction (the erythema) was scored by measuring skin color with an electronic instrument, the Minolta Chromameter. The experiment was repeated twice, on two different individuals. In all cases, with both drugs, it was found that ammonium chloride significantly reduced the irritant reaction. Representative results (means of Chromameter reading±SEM at different times after removal of gels) are shown in FIGS. 3a and 3b.

EXAMPLE 6

The in vitro permeation through human skin of chloroquine from the gels of Example 5, with and without ammonium chloride, was determined.

Circular pieces of human epidermis were mounted in horizontal permeation cells (1.13 cm$^2$ of effective permeating surface) with the stratum corneum facing the donor compartment of the cell. A known volume (20–23 ml) of 0.2 M TRIS buffer pH 7.5 (the receptor solution) was placed in the receptor compartment. The cell was then placed in a water bath-shaker at 37° C. and allowed to equilibrate. A 0.2 ml aliquot of the tested formulation was transferred to the donor compartment. Occlusion was achieved by the use of a teflon film in contact with the formulation. At 3, 8 and 24 hours, the receptor solutions were removed and replaced with equal volumes of fresh receptor solution previously equilibrated at 37° C. Chloroquine was quantified in the samples by fluorometrical measurements. These were carried out at rom temperature in a Perkin-Elmer LS-5B luminescence spectrometer. The samples were adjusted to pH 8.65 at a final TRIS concentration of 0.1 M and 30% (vol/vol) ethanol. The excitation wavelength was 333 nm and the emission wavelength was 382 nm. Chloroquine concentrations were extrapolated by comparison with a standard curve obtained under the same conditions. These data were used to calculate the cumulated amount of chloroquine that permeated through the skin at the indicated times. For each formulation condition, eight permeation cells were used. Results are presented as the means with their associated standard error.

Figure 4:
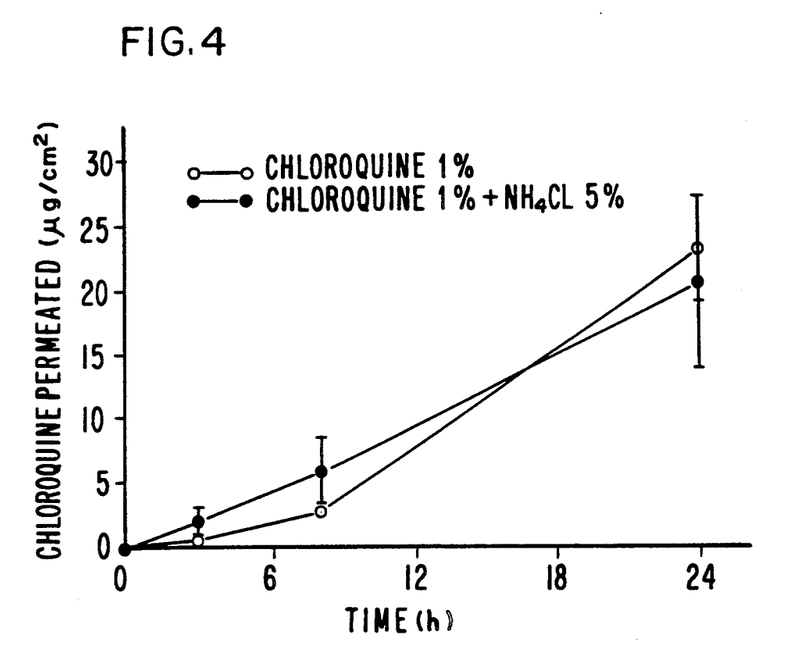
FIG. 4 is a graph which shows the flux through human epidermis of chloroquine alone or with ammonium chloride.

The permeation was found to be the same whether in the presence or the absence of ammonium chloride, as illustrated in FIG. 4. This indicates that the reduction in irritation shown in Example 5 wa snot a result of less drug being present in the skin.

EXAMPLE 7

The decrease in the in vivo skin irritation of chloroquine by the addition of an ionophore, monensin, was shown.

Following the procedures of Example 5, chloroquine-containing (1.0 wt %) gels were prepared with and without monensin (5.0 wt %) and were tested on adult males. It was found that monensin reduced the irritant reaction, as is shown in FIG. 3b.

While this invention has been described in detail with particular reference to certain preferred embodiments thereof, it will be understood that variations and modifications can be effected without departing from the spirit and scope of the invention as defined in the appended claims.

What is claimed is:

1. A method of reducing or preventing human skin irritation during transdermal administration to a human of a weak base drug, which drug is capable of accumulating in the lysosomes and is susceptible to inducing skin irritation in the human when the drug is transdermally administered, the method comprising coadministering to a selected site on the skin or mucosa of the human:
   (a) a therapeutically effective amount of the weak base drug, at a therapeutically effective rate over a predetermined period of time; and
   (b) an effective amount of a lysosomal uptake-inhibiting agent capable of inhibiting the lysosomal uptake of the drug to reduce or prevent irritation to the skin or mucosa, the amount of the lysosomal uptake-inhibiting agent being from 0.01 wt % to 20 wt % of the drug/agent composition.

2. A method according to claim 1 wherein the drug and the agent are coadministered transdermally from a matrix placed in drug and agent transmitting relation with the skin or mucosa.

3. A method according to claim 1 wherein the agent is an ionophore.

4. A method according to claim 3 wherein the agent is an monensin.

5. A method according to claim 3 wherein the ionophore is present in an amount of from 0.01 wt % to about 5 wt %.

6. A method according to claim 1 wherein the agent is a weak base competitor compound.

7. A method according to claim 6 wherein the agent is an amphiphilic amine.

8. A method according to claim 7 wherein the agent is chosen from ammonia and its salts, small molecular weight amines and their salts and aminoalcohols.

9. A method according to claim 8 wherein the agent is ammonium chloride.

10. A method according to claim 6 wherein the weak base competitor compound is present in an amount of from 0.2 wt % to about 20 wt %.

11. A method according to claim 1 wherein the drug is propranolol and the agent is monensin or ammonium chloride.

12. A method according to claim 1 wherein the drug is chloroquine and the agent is monensin, (R)(+)−1,1'-bi-2-naphthol, nigericin, valinomycin, gramicidin D, nonactin, A23187, carbonyl cyanide m-chlorophenylhydrazone, ammonium chloride, diethylamine, isopropylamine, ethanolamine, diethanolamine, triethanolamine or tromethamine.

13. A method according to claim 1 wherein the drug is selected from clemastine, imipramine, chlorpromazine and quinacrine, and the agent is monensin.

14. A transdermal drug delivery device for transdermally administrating a weak base drug to a human, which drug is capable of accumulating in the lysosomes and is susceptible to inducing skin or mucosal irritation in the human when the drug is transdermally administered, the device comprising:
   (a) a matrix adapted to be placed in drug and lysosomal uptake-inhibiting agent transmitting relation with a selected site on the skin or mucosa of the human, the matrix containing sufficient amounts of drug and lysosomal uptake-inhibiting agent to continuously and co-extensively administer to the skin or mucosal site:
(1) a therapeutically effective amount of the weak base drug, at a therapeutically effective rate over a predetermined period of time; and
(2) an effective amount of a lysosomal uptake-inhibiting agent capable of inhibiting the lysosomal uptake of the drug to reduce or prevent irritation to the skin or mucosa, the amount of the lysosomal uptake-inhibiting agent being from 0.01 wt % to 20 wt % of the drug/agent composition.

15. A method according to claim 14 wherein the agent is an ionophore.

16. A method according to claim 15 wherein the agent is an monensin.

17. A method according to claim 15 wherein the ionophore is present in an amount of from 0.01 wt % to about 5 wt %.

18. A method according to claim 14 wherein the agent is a weak base competitor compound.

19. A method according to claim 18 wherein the agent is an amphiphilic amine.

20. A method according to claim 19 wherein the agent is chosen from ammonia and its salts, small molecular weight amines and their salts and aminoalcohols.

21. A method according to claim 20 wherein the agent is ammonium chloride.

22. A method according to claim 18 wherein the weak base competitor compound is present in an amount of from 0.2 wt % to about 20 wt %.

23. A method according to claim 14 wherein the drug is propranolol and the agent is monensin or ammonium chloride.

24. A method according to claim 14 wherein the drug is chloroquine and the agent is monensin, (R)(+)−1,1′-bi-2-naphthol, nigericin, valinomycin, gramicidin D, nonactin, A23187, carbonyl cyanide m-chlorophenylhydrazone, ammonium chloride, diethylamine, isopropylamine, ethanolamine, diethanolamine, triethanolamine or tromethamine.

25. A method according to claim 14 wherein the drug is selected from clemastine, imipramine, chlorpromazine and quinacrine, and the agent is monensin.

* * * * *